United States Patent [19]

Van der Knaap

[11] Patent Number: Plant 6,303

[45] Date of Patent: Sep. 20, 1988

[54] CHRYSANTHEMUM PLANT NAMED GOLDEN BIJOUX

[75] Inventor: Jacques C. M. Van der Knaap, De Lier, Netherlands

[73] Assignee: Fides Beheer B.V., De Lier, Netherlands

[21] Appl. No.: 915,108

[22] Filed: Oct. 3, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Golden Bijoux particularly characterized by its yellow tubular ray floret color; green to yellow disc floret color; vigorous growth habit; nine week response; spider/anemone capitulum form, and by its excellent flower production.

1 Drawing Sheet

The present invention comprises a new and distinct cultivar of Chrysanthemum, botanically known as *Chrysanthemum morifolium*, Ramat., and referred to by the cultivar name Golden Bijoux.

Golden Bijoux was discovered by applicant in 1983 as a spontaneous mutation of Bijoux, a cultivar of applicant disclosed in a pending application.

Golden Bijoux was the result of an induced radiation program conducted by applicant in De Lier, The Netherlands, in 1983. Plants of the parent cultivar Bijoux were subjected to radiation levels of 1750 rad X-rays. Golden Bijoux was discovered and selected as a mutation by virtue of its generally yellow spoon and tube color, as opposed to the pink spoon and tube color of Bijoux. The disc floret color of Golden Bijoux was also noticed as being significantly different than its parent. Subsequent development of the new cultivar indicated that Golden Bijoux is also more vigorous than its parent.

The first act of asexual reproduction of Golden Bijoux was accomplised when vegetative cuttings were taken from the initial selection in 1983 in a controlled environment in De Lier, The Netherlands by a technician working under formulations established and supervised by Jacques C. M. Van der Knaap. Horticultural examination of selected units initiated in 1983 has demonstrated that the combination of characteristics as herein disclosed for Golden Bijoux are firmly fixed and are retained through successive generations of asexual reproduction.

Golden Bijoux has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Golden Bijoux which, in combination, distinguish this Chrysanthemum as a new and distinct cultivar:

1. Spider/anemone capitulum form.
2. Yellow tubular ray floret color.
3. Green (immature to yellow (mature) disc floret color.
4. Nine week response.

5. Excellent flower production per stem.
6. 60 mm diameter across face of capitulum.
7. Vigorous growth habit.
8. The cushion of disc florets is somewhat raised but not as much as its parent Bijoux or the other sports of Bijoux. Moreover, fewer or hardly any petaloids are formed and those that are formed are generally the same color as the mature disc florets.

The accompanying photographic drawing shows typical inflorescence and foliage characteristics of Golden Bijoux, with the color being as close as possible in photographs of this type.

In the following description, color references are made to The Royal Horticultural Society Colour Chart. The color values were determined in August 1986 under natural daylight at De Lier, The Netherlands.

Classification:

*Botanical.*—*Chrysanthemum morifolium*, Ramat., cv. Golden Bijoux.

*Commercial.*—Spider/anemone spray.

INFLORESCENCE

A. Capitulum:
- *Form.*—Flat.
- *Type.*—Spider/anemone.
- *Diameter across face.*—60 mm.

B. Corolla of ray florets:
- *Color (general tonality from a distance of three meters).*—Yellow with green-yellow disc floret center.
- *Color (tube).*—8A.
- *Color (upper surface of spoon).*—16C.

C. Corolla of disc florets:
- *color (mature).*—13C.
- *Color (immature).*—154C.

D. Reproductive organs:
- *Androecium.*—Only rudimentary in disc florets.
- *Gynoecium.*—Present in both ray and disc florets.

PLANT

A. General appearance:
- *Height.*—80 cm.

B. Foliage:
- *Color (upper surface).*—147B.
- *Color (under surface).*—147A.
- *Shape.*—Medium to long, lobed and finely serrated.

C. Growth habit.—Very vigorous.

I claim:

1. A new and distinct Chrysanthemum plant named Golden Bijoux, as described and illustrated, and particularly characterized by its yellow tubular ray floret color; green to yellow disc floret color; vigorous growth habit; nine week response; spider/anemone capitulum form, and excellent flower production.

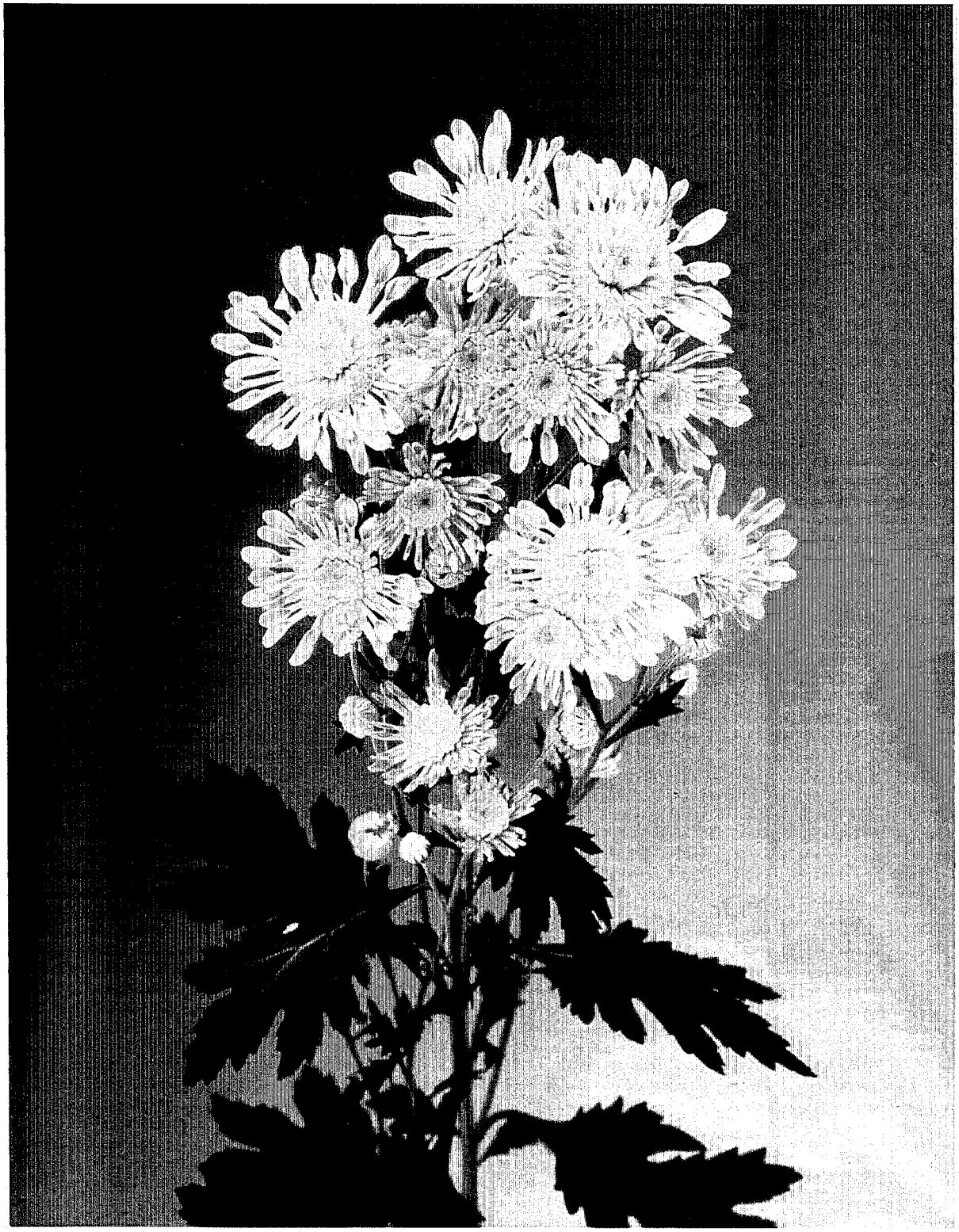

* * * * *